United States Patent [19]
Bustamante et al.

[11] Patent Number: 4,881,818
[45] Date of Patent: Nov. 21, 1989

[54] DIFFERENTIAL IMAGING DEVICE

[75] Inventors: Carlos Bustamante; Frederick K. Husher; David Beach, all of Albuquerque, N. Mex.

[73] Assignee: The University of New Mexico, Albuquerque, N. Mex.

[21] Appl. No.: 855,006

[22] Filed: Apr. 22, 1986

[51] Int. Cl.[4] ............................................. G01N 21/21
[52] U.S. Cl. .................................... 356/367; 356/364
[58] Field of Search ............... 356/364, 365, 366, 367, 356/368, 444

[56] References Cited

U.S. PATENT DOCUMENTS

| | | | |
|---|---|---|---|
| 3,525,803 | 8/1970 | Smart | 356/867 |
| 3,586,443 | 6/1971 | Hooper | 356/365 |
| 3,602,597 | 8/1971 | Sproul | 356/365 |
| 3,612,688 | 10/1971 | Liskowitz | 356/364 |
| 3,817,634 | 6/1974 | Barron et al. | 356/364 |
| 3,943,369 | 3/1976 | Saeva | 250/568 |
| 3,967,902 | 7/1976 | Steinberg | 356/364 |
| 3,992,571 | 11/1976 | Garlick et al. | 356/365 |
| 4,203,670 | 5/1980 | Bromberg | 356/367 |

OTHER PUBLICATIONS

Schnepp et al, "The Measurement of Circular Dichroism in the Vacuum Ultraviolet", *The Review of Scientific Instruments*, vol. 41, No. 8, Aug. 1970, pp. 1136-1141.
M. F. Maestre and J. E. Katz, "A Circular Dichroism Microspectrophotometer", Biolpolymers, vol. 21, 1899-1908 (1982).

*Primary Examiner*—Richard A. Rosenberger

[57] ABSTRACT

An apparatus for forming a differential image of a specimen is disclosed. The two images whose difference is used to generate the differential image are made by illuminating said specimen with polarized light, each image corresponding to illuminating the specimen with light of a different polarization. The intensity of the differential image at each point is related to the difference in intensities observed when the point in question is illuminated with light having the different polarizations divided by the sum of said observed intensities. The present invention includes a light source for illuminating the image with polarized light having a polarization which oscillates between first and second preselected states of polarization, said oscillations occurring at a predetermined frequency. The intensity of light leaving each of a preselected plurality of points on the specimen is measured as a function of time by a light detecting apparatus which generates an electrical signal which is related to the intensity of light at the preselected point in question. This electrical signal is used as input to a lock-in amplifier referenced to said predetermined frequency. The output of this amplifier is related to the difference in intensity of the two images at the preselected point in question. The present invention measures the output of the lock-in amplifier and the time averaged input signal to the lock-in amplifier at each of the preselected points and displays the ratio of said output to the time averaged input to the lock-in amplifier as a two dimensional image.

1 Claim, 3 Drawing Sheets

DIFFERENTIAL IMAGING DEVICE

The U.S. Government has rights in this invention pursuant to National Institute of Health Grants 3254 and GM 32546.

BACKGROUND OF THE INVENTION

The present invention relates generally to the field of imaging, and more specifically, to imaging techniques in which an image is generated from the difference of two images made with light of different polarizations.

An image may be defined to be a mapping of the spatial distribution of some property of the specimen being imaged into another spatial distribution of the property or of a different property. For example, a typical black and white photographic negative of an object is a mapping of the spatial distribution of the intensity of light leaving each point on the object. The mapping process consists of setting the density of silver grains at each point in the negative in proportion to the intensity of light leaving the corresponding point on the specimen.

Imaging systems based on the mapping of a number of different physical properties are well known to the prior art. Such systems typically employ some form of electromagnetic radiation to probe the sample being imaged. For example, an x-ray image is a mapping of the ability of each point in the imaged part of the specimen to absorb electromagnetic radiation in the x-ray frequency range. A simple NMR image of a patient is a mapping of the hydrogen ion density at each point in a plane intersecting the patient's body.

Images of many biological specimens of interest are difficult to obtain because the structures one wishes to image do not significantly differ from the surrounding structures in their absorbance of electromagnetic radiation. For example, protein and DNA have similar densities and gross chemical compositions; hence it is difficult to distinguish one from the other using imaging based on the absorption of light.

One prior art solution to imaging biological specimens is to stain the specimen with a specific stain which binds to the structure of interest and which is easily imaged. For example specific stains have been developed which bind to specific proteins. These stains are typically constructed by combining a monoclonal antibody with a chromophore which is easily detected using light of a specific frequency. Although such staining systems provide greatly improved images in those cases in which they are applicable, they typically provide only information about the concentration of the particular protein to which the antibody binds. No information is provided about the orientation of the protein in question or its organization into larger structures unless the organization alters the density of the protein molecules significantly. Such staining systems also may produce artifacts resulting from the disruption of the specimen needed to introduce the staining agent or from the non-preferential binding of the stain to other structures in the specimen. In addition, a specific stain must be made for each imaging problem, which involves considerable time and expense.

Further, in a large number of imaging problems, one does not know in advance the best parameter to use to construct an image which distinguishes two specimens, one normal and one abnormal. If the two specimens differed in the concentration of some known compound, an imaging system based on a stain might be possible. However, in general, no such compound is known in advance and, hence, one is left to try a number of different imaging modalities in an attempt to find one that distinguishes the two specimens. This will be especially difficult if the two specimens differ mainly in the organization of some compound rather than in its concentration.

In principle, organizational differences may be detected using polarized light. A structure in the image composed of molecules which are bundled with a specific orientation will absorb light of one polarization in preference to light of another polarization. Hence an image formed by subtracting a first image taken with polarized light having one linear polarization from a second image taken with polarized light having a different linear polarization will often display such structures.

Similarly, man biological molecules of interest are chiral in nature. A chiral structure is one whose mirror image is different from the image of the structure. For example, helical molecules such as DNA are either left or right handed depending on the twist of the helix. The mirror image of a right handed helix is a left handed helix, not a right handed helix. Such molecules preferentially absorb circularly polarized light of one handedness. Hence an image formed from the difference of two images, one taken with right handed circularly polarized light and the other taken with left handed circularly polarized light will, in principle, display the concentration of such molecules.

Such differential image techniques also find application in the material sciences. For example, strains in transparent materials such as glass may be detected with polarized light. Here, specific staining techniques are of little value.

Unfortunately, the magnitude of the difference of the absorbance of circularly polarized light of different handedness for most biological specimens is quite small at wavelengths in the optical region of the light spectrum. Often, to measure this difference in the visible region of the spectrum, each of the images must be measured to an accuracy of the order of one part in ten thousand. In principle, one could increase this difference by using smaller wavelength light. The maximum difference in absorbance occurs at wavelengths which are of the same length as the diameter of the molecules or structures being imaged. Thus to obtain the maximum difference for chiral molecules, circularly polarized light in the x-ray region of the spectrum is needed. However, circularly polarized light sources in this region of the spectrum are not economically practical.

Prior art systems which attempt to exploit this type of differential imaging are often limited by the sensitivity of the detector used to form the two images which are subtracted. For example, if a standard television camera tube is used to record each of the images, differences which are less than a few percent of the light intensity of each image may not be detected. This limit is imposed by the small dynamic range of the television camera and by the electronic noise in the camera and the subsequent amplifiers. Hence it is difficult to apply this type of imaging technique to biological samples unless large concentrations of chiral molecules are present or unless large ordered structures are being imaged.

Broadly, it is an object of the present invention to provide an improved system for producing images which are the difference of two images made using light of different polarizations.

It is a further object of the present invention to provide an imaging system which can detect differences of less than one part in a thousand in the two images.

These and other objects of the present invention will become apparent from the following detailed description of the invention and the accompanying drawings.

SUMMARY OF THE INVENTION

The present invention comprises an apparatus for forming a differential image of a specimen. The two images whose difference is used to generate the differential image are made by illuminating said specimen with polarized light, each image corresponding to illuminating the specimen with light of a different polarization. The intensity of the differential image at each point is related to the difference in intensities observed when the point in question is illuminated with light having the different polarizations divided by the sum of said observed intensities. The present invention includes a light source for illuminating the image with polarized light having a polarization which oscillates between first and second preselected states of polarization, said oscillations occurring at a predetermined frequency. The intensity of light leaving each of a preselected plurality of points on the specimen is measured as a function of time by a light detecting apparatus which generates an electrical signal which is related to the intensity of light at the preselected point in question. This electrical signal is used as input to a lock-in amplifier referenced to said predetermined frequency. The output of this amplifier is related to the difference in intensity of the two images at the preselected point in question. The present invention measures the output of the lock-in amplifier and the time averaged input signal to the lock-in amplifier at each of the preselected points and displays the ratio of said output to the time averaged input to the lock-in amplifier as a two dimensional image.

DETAILED DESCRIPTION OF THE INVENTION

Figure 1:
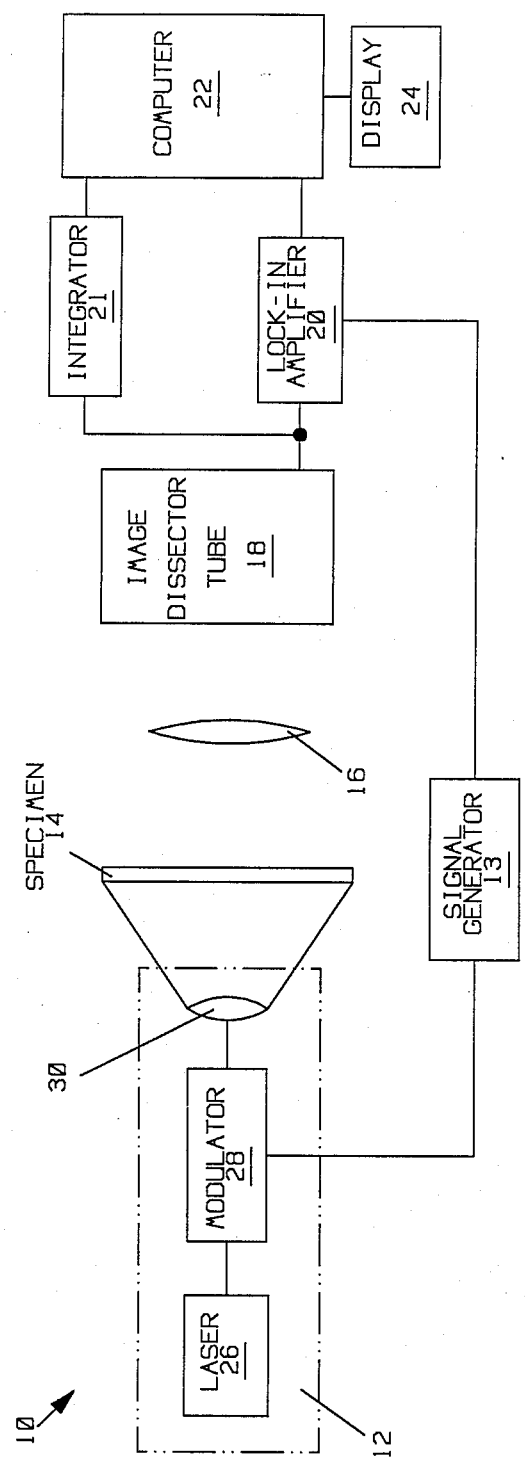
FIG. 1 illustrates an imaging apparatus according to the present invention.

Prior art differential imaging systems are limited by the dynamic range and/or the signal to noise ratio of the detectors and electronics used to measure the intensity of each of the images used in forming the differential image in question. Each of these factors introduces an uncertainty into the measured images used to construct the differential image. Since the differential image is the result of subtracting two measured images, even a small error can lead to large uncertainties in the differential image. For example, if the measured images have uncertainties of only 1%, a differential image formed by subtracting two images which differ from each other by 10% may have an uncertainty of as much as 20%. Hence it is important to reduce the uncertainties in each image.

Electronic noise typically results from two sources. First, the image detecting apparatus which transforms the light leaving a specified point on the specimen into an electrical signal introduces noise. For example, if the image detector includes a photomultiplier stage, thermally emitted electrons from the dynodes result in noise being added to the output signal. Second, the output of the image detecting apparatus often must be amplified and the amplification stages used for this purpose also introduce noise.

Uncertainties also result from a lack of dynamic range in the image detector. For example, image detection systems based on vidicon tubes are inherently limited to measuring images which differ by at least one percent. Such tubes typically provide only 256 gray levels, i.e., there is an uncertainty of 1 part in 256 in the light intensity measured at each pixel of the image. Hence the difference of two images measured with such detectors may include an uncertainty as large as 2 parts in 256 from the limited dynamic range of the detector in addition to the uncertainties arising from the various noise sources. In addition, if the images are digitized before being subtracted to form the differential image, the digitization process itself may introduce an error of the order of half of a gray level in each image. Such an error may be significant if the images differ by only a small amount. In principle, one can avoid this type of dynamic range uncertainty by using an image detector with a with higher dynamic range such as an image dissector tube and digitizing the signal to a much higher number of gray levels. However, the signal to noise ratio of the image dissector tube and the electronics used to process the signal from the image dissector tube introduce an uncertainty which limits the usefulness of such systems in differential imaging applications. In principle, the contribution to the uncertainty in the image resulting from the electronic noise may be substantially reduced by averaging each of the images used to form the differential image over a sufficiently long period of time. However, in practice, the time required is too long to be practical.

The present invention avoids these limitations by combining a high dynamic range image detection system with a polarization modulated light source. The polarization modulated light source illuminates the specimen with light having a polarization which oscillates at a predetermined frequency between two predetermined states of polarization. Hence the signal from the image detection system which represents the intensity of light leaving the specimen has a DC component which is related to the sum of the two images used in forming the differential image and an AC component at said predetermined frequency which is related to the difference of the two images in question. The differential image is constructed by displaying the ratio of the AC component to the DC component for each point on the specimen. Since the noise in the image dissector tube and subsequent electronics has a frequency distribution which is much broader than that of the desired AC component, a substantial improvement in signal to noise ratio may be obtained by measuring only that part of the AC signal having a frequency in a narrow band of frequencies centered at the predetermined frequency in question.

Such a system is shown schematically at 10 in FIG. 1. A polarization modulated light source 12 in which the polarization of the light oscillates between first and second states of polarization in response to signals from a signal generator 13 is used to illuminate a specimen 14. The light leaving the specimen 14 is imaged by a lens 16 onto the photocathode of an image dissector tube 18.

This results n an image of the specimen being formed on the photocathode of the image dissector tube 18. The output of the image dissector tube 18 is coupled to a lock-in amplifier 20 which is referenced to the frequency of oscillation of the polarization modulated light source 12. The input to the lock-in amplifier 20 is time averaged by an averaging circuit 21. The averaging time is chosen to be sufficiently long to average out the AC component of the signal from the image dissector tube. An averaging time constant of 10 periods of the AC signal is sufficient. Both the output and time-averaged input to the lock-in amplifier are connected to a computer 22 which forms the ratio of these two signals. This ratio is used to construct the differential image which is displayed on a display terminal 24. The differential image is measured one point at a time. The point in question is selected by applying appropriate deflection potentials to the image dissector tube 18 which is under the control of the computer 22. The computer 22 causes the image dissector tube 18 to scan each of a plurality of image points and then displays the ratio of output of the lock-in amplifier 20 to the time averaged input signal to the lock-in amplifier 20 as a function of the locations of these image points on the image dissector tube photocathode using the display terminal 24 or other graphic output system. Since the lock-in amplifier 20 amplifies only that portion of the input signal which is in a narrow band of frequencies centered at the reference frequency, the contribution of the noise to the uncertainty in the measured image is significantly reduced my modulating the light source.

In addition, the difference of the two images is directly measured The present invention forms the difference of the two images and then digitizes said difference. Hence separate digitization of each image followed by subtraction of the two images is not needed. This reduces the image processing and reduces the uncertainties in the differential image introduced by the digitization process.

In the preferred embodiment, the polarization modulated light source consists of a laser 26, a polarization modulator 28, and a lens system 30. The laser 26 produces a beam of polarized light having a constant polarization. The polarization of the laser light is modified by the polarization modulator 28 in response to electrical signals applied to the polarization modulator 28 by a signal generator 13. The lens system 30 is used to expand the beam of light leaving the polarization modulator 28 such that the entire specimen is illuminated. It will be apparent to those skilled in the art that the laser may be replaced by a non-polarized light source and a polarizer which removes light of all but one desired polarization.

The laser beam enters the polarization modulator 28 parallel to one axis of the polarization modulator, designated herein as the z-axis. The actual modification is accomplished by changing the refractive index of a polarization modulator medium along one axis perpendicular to the z-axis, e.g., the x-axis, relative to the a second axis, e.g.,the y-axis, which is also perpendicular to the z-axis. This anisotropy in the refractive index results in the polarization of the laser beam being altered. By varying the anisotropy in time, a beam having a polarization which oscillates between two predetermined states of polarization may be obtained. For example, the polarization may be oscillated between left handed circularly polarized light and right handed circularly polarized light or between vertically polarized linearly polarized light and horizontally polarized linearly polarized light.

The use of a polarization modulator to change the polarization of light is well known to those skilled in the optical arts. The preferred polarization modulator is a photoelastic modulator of the type described by Kemp in U.S. Pat. No. 3,867,014 which is hereby incorporated by reference. This type of modulator produces the anisotropy in question by applying stress to a plate made of an isotropic material such as glass using transducers which convert an electrical signal into a acoustical vibration in the plate. This type of polarization modulator is preferred because the resulting polarization varies in a sinusoidal manner between the two predetermined states of polarization. Hence the AC component of the signal from the image dissector tube 18 will also be sinusoidal with a frequency at the predetermined frequency of the signal generator 13.

It will be apparent to those skilled in the art that other types of polarization modulators may be used. For example, a Pockels' Cell which typically consists of a suitable crystal, such as potassium dideuterium phosphate ($KD_2PO_4$) and a means for applying an electric field may be used. By choosing the angle of incidence of the light on the crystal and the applied voltage, light of different polarizations may be produced. This effect is discussed in detail in "Circular Dichroism-Theory and Instrumentation", Analytic Chemistry, Vol. 38, p. 29a, June 1966, which is hereby incorporated by reference. The state of the polarization of the light leaving the Pockels' Cell is caused to oscillate between first and second polarization states by applying an appropriate oscillating potential to the Pockels' Cell using the signal generator 13. In the preferred embodiment, the two states in question are left and right handed circularly polarized light. However, embodiments in which the two states correspond to other polarization states such as two linearly polarized states will be apparent to those skilled in the art.

In the preferred embodiment, light leaving each of the points on the specimen which is to be included in the image is imaged onto the photocathode of an image dissector tube 18 by a lens 16. An image dissector tube consists essentially of a photocathode, a deflection system for accelerating and directing photo-electrons leaving the photocathode at a specified location through a pin-hole, and a photomultiplier section for amplifying the photoelectron current passing through said pin-hole. The location from which photo-electrons will be selected for amplification is determined by signals to the deflection system. Hence the image dissector tube provides both a means for selecting a point on the specimen to be examined and for developing an electrical signal related to the intensity of light leaving said point.

An image dissector tube is preferred because it has a larger dynamic range than presently available vidicon tube and because its output is not time averaged. As noted above, the typical vidicon tube has less than 1000 gray levels. An image dissector tube may have as many as 10,000 gray levels. The preferred embodiment image dissector tube is an ITT F4100RP.

Vidicon tubes also time average the image which make such image detectors unsuitable for use in the present invention. The present invention requires that the image detector provide a signal which represents the light intensity as a function of time for each point on the specimen in the field of view. As pointed out above, this signal will have a DC component which represents the sum of the two images of the specimen used in generating the differential image and an AC component at the frequency of the polarization modulated light source which represents the difference in light intensity which would be observed if the point in question on the specimen was first illuminated with light having the first state of polarization and then with light having the second state of polarization. This AC component is related to the output of the lock-in amplifier 20. This AC component will be lost if the image detector averages this signal over a time of the order of the time between changes in the state of polarization. That is, the image detector can at most average the signal over a time which is small compared to the period of the oscillation of polarization modulated light source. It is preferred that the detector not average the signal over a time longer than one tenth the period of the polarization modulated light source frequency. In the preferred embodiment, the polarization modulated light source frequency is 50 KHz. Hence the image detector must not time average the signal over a time longer than 2 microseconds.

In a typical vidicon tube, a light image on the photocathode results in a charge being stored on the photocathode. After sufficient charge has accumulated, the charge is read-out by scanning the photocathode with an electron beam in a raster scan. The vidicon signal is related to the current which must be supplied at each point on the photocathode by this electron beam to neutralize the charge stored on the photocathode. This signal represents the total light which was received by each point on the photocathode surface since that point was last read-out. Since the vidicon is typically read-out one frame at a time, to be suitable for use in the present invention, a vidicon tube would need to have a read-out speed of one frame every 2 microseconds which is not realizeable with currently available vidicon tubes.

In principle this problem could be overcome by reducing the frequency at which the polarization modulated light source oscillates. However, it should be noted that most noise sources have a frequency dependence. For example, the amplitude of the noise signal typically decreases as the inverse of the frequency in many amplifiers. Hence if the oscillation frequency is reduced to prevent the signal from being averaged over a time which is a significant fraction of the oscillation period, the signal to noise ratio of the differential measurement may also be significantly reduced.

Figure 2:
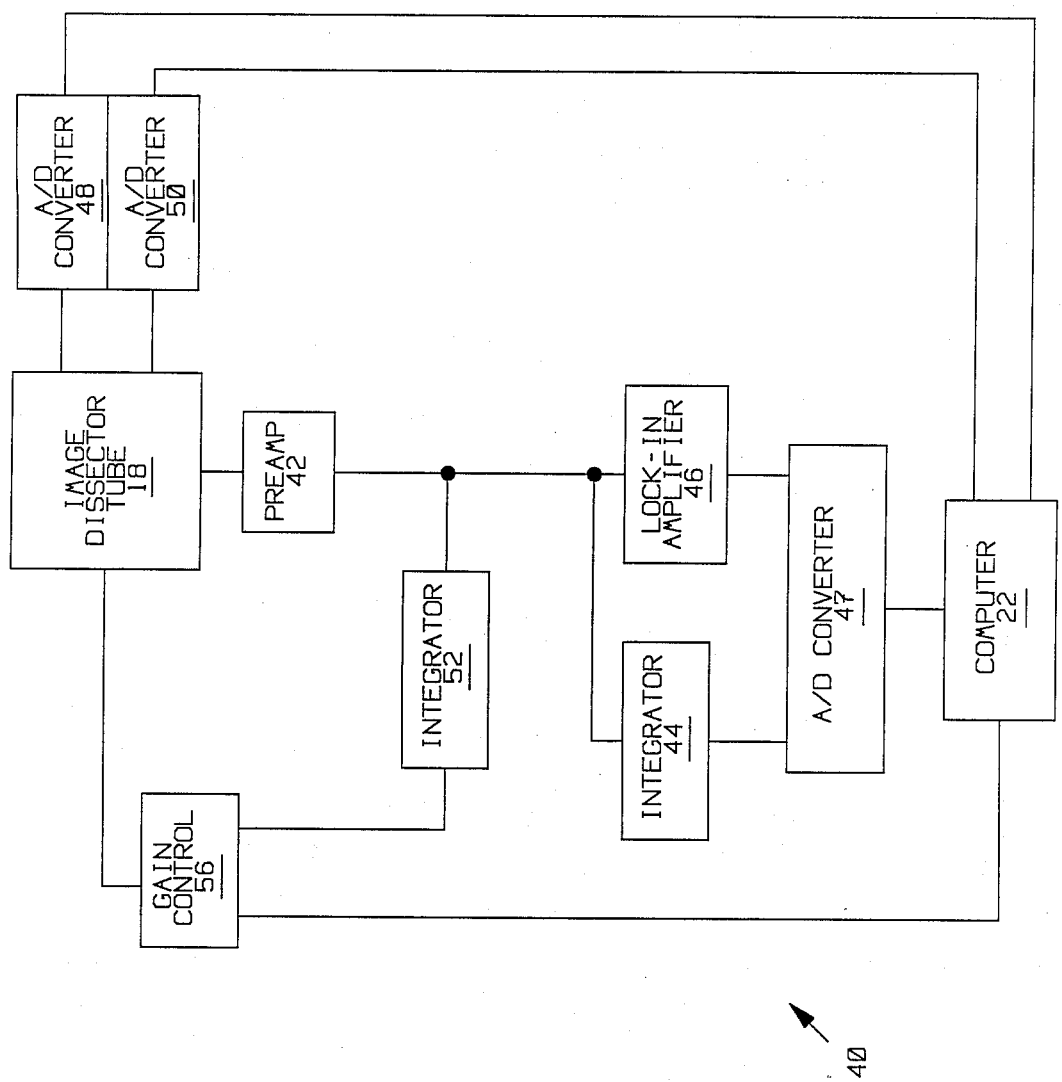
FIG. 2 is a block diagram of the preferred embodiment of the electronics associated with the image dissector tube shown in FIG. 1.

A block diagram of the preferred embodiment of the image dissector tube and its associated electronics are shown in FIG. 2 at 40. The output of the image dissector tube 18 is amplified by a preamplifier 42 which matches the output impedance of the image dissector tube 18 to the remainder of the electronics. The output of the preamplifier 42 is fed to a first integrator 44 and a lock-in amplifier 46. The output of the first integrator 44 is related to the DC component of the signal from the image dissector tube 18. It is digitized in an analog to digital converter 47 which is under the control of the computer 22. The output of the lock-in amplifier is related to the difference in the two images in question. It is also digitized by the analog to digital converter 47. The position of the point on the photocathode of the image dissector tube from which photoelectrons are selected for amplification is specified by signals from the computer 22 to two digital to analog converters 48 and 50 which apply the appropriate analog voltages to the deflection system of the image dissector tube 18.

The image dissector tube 18 includes a photomultiplier chain which has a gain which may be controlled by the voltages applied to the dynodes which make-up said photomultiplier chain. For reasons that will be explained below, this gain section is adjusted to provide a constant output from the image dissector tube 18. This is accomplished by integrating the output of the preamplifier 42 in a second integrator 52. The output of the second integrator 52 is used to control an automatic gain control circuit 56 which varies the voltages on the first three dynodes in the image dissector tube photomultiplier chain so as to cause the output of the preamplifier 42 to match a coarse gain level supplied by the computer 22.

In order to form an image, the computer causes the image dissector tube 18 to scan a predetermined sequence of points on the photocathode of the image dissector tube. The total light intensity leaving successive points may vary significantly if the points in question correspond to points on the specimen having markedly different absorption or scattering. If the image dissector tube gain is not changed, this difference in light intensity can result in a significant delay in measurement time because the lock-in amplifier 46 has a finite settling time. In addition, the different signal levels result in different noise levels in the lock-in amplifier which could limit the sensitivity of the system. By adjusting the gain of the photomultiplier section of the image dissector tube 18 in response to the change in light level, these artifacts are minimized. It should be noted that the measured image is independent of the gain of the system, since each pixel in the image is the ratio of a difference in measured intensities to the average intensity. That is, since each of the parameters is proportional to the gain of the image dissector tube, their ratio is independent of said gain.

Figure 3:
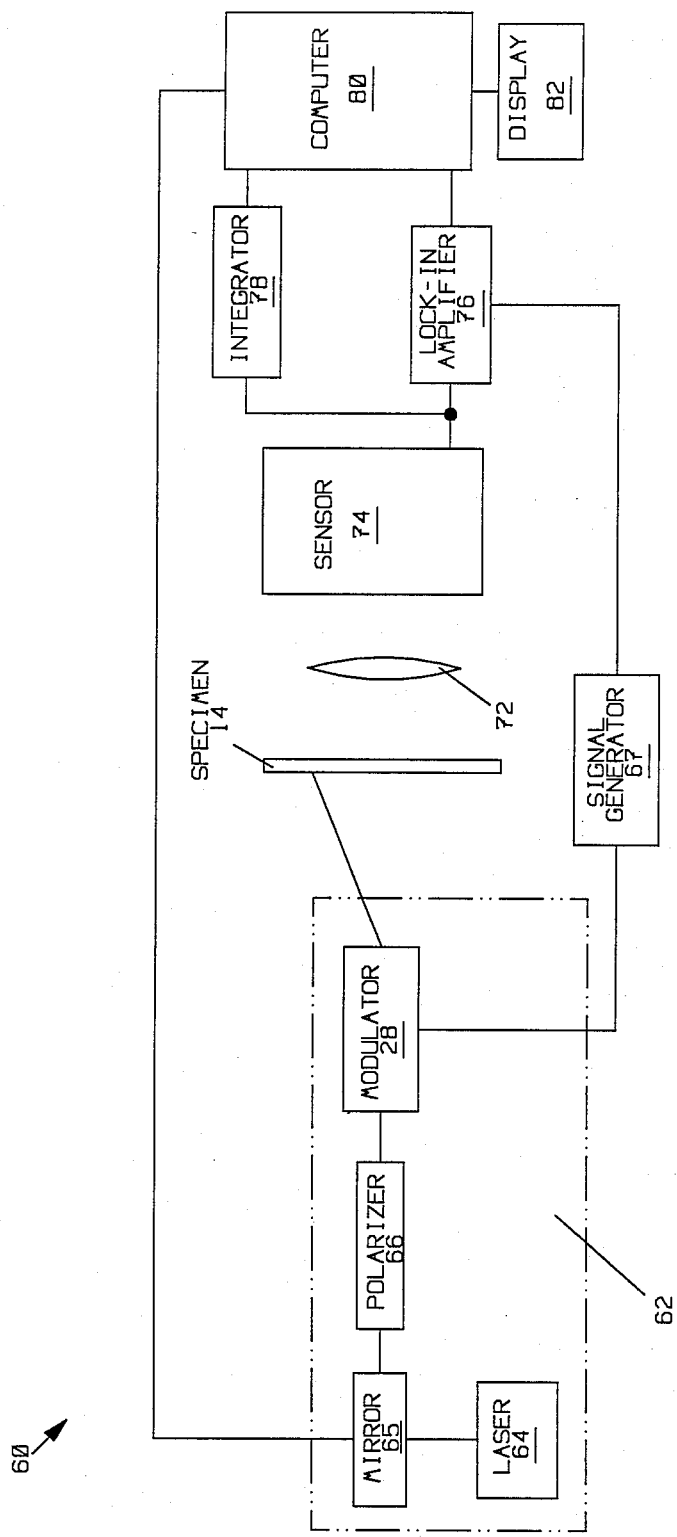
FIG. 3 illustrates an alternate embodiment of an imaging apparatus according to the present invention which employs a non-imaging light sensor.

It will be apparent to those skilled in the art that the image dissector tube 18 may be replaced by a non-scanning light sensing device such as a photomultiplier tube or photodiode and a means of directing the light from a specified point on the specimen into the light sensor in question. Such an alternative embodiment is shown in at 60 in FIG. 3. It employs a mechanical scanning system and non-scanning light sensor. In this embodiment, only the point on the specimen which is currently being scanned is illuminated by the polarization modulated light source. The polarization modulated light source 62 consists of a laser 64, a moveable mirror 65, a fixed polarizer 66, and a polarization modulator 68. The mirror 65 includes a means of adjusting the angle of incidence of the laser beam thereon to produce a deflected laser beam directed at a specified point on the surface of the specimen 14. The adjustment means is under the control of the computer 80. The adjustment means may be two stepping motors or similar actuators such as pizo-electric driven stages. The reflection of the laser light by the mirror will in general alter the light's polarization. Hence, the deflected beam is passed through a fixed polarizer 66 which assures that the light entering the polarization modulator 68 has a polarization which is independent of the angle through which the light was deflected by the mirror 65. The light leaving the specimen is collected by a lens 72 and imaged onto a light sensor 74 which is preferably a photomultiplier tube. The output of the light sensor is coupled to a lock-in amplifier 76 which is referenced to the polarization modulated light source frequency and to an integrator 78. The integrator 78 and lock-in amplifier 76 are connected to a computer 80 which assembles the image and controls the point of illumination on the specimen by signals to the positioning means 68. The computer 80 accumulates data representing the differential image at the various points of interest on the specimen and displays these on a display terminal 82 in a manner analogous to that described with reference to FIG. 1 above.

It will be apparent to those skilled in the art that the photomultiplier tube may be replaced by any light detector having a response time which is short compared to the period of oscillation of the polarization modulated light source. For example, a photodiode may be used.

It will also be apparent to those skilled in the art that the apparatus taught by the present invention may also be used with electro-magnetic radiation outside the visible light region. Hence the term "light" as used in this application is defined to include electro-magnetic radiation outside the visible spectrum as well as visible light.

Various modifications to the present invention will become apparent to those skilled in the art from the foregoing description and accompanying drawings. Such modifications are intended to fall within the scope of the appended claims.

What is claimed is:

1. An apparatus for forming a differential image of a specimen comprising:

means for illuminating said specimen with polarized light having a polarization which oscillates between a first preselected state of polarization and a second preselected state of polarization, said oscillation occurring at a predetermined frequency;

means for detecting the intensity of light leaving a selected point on said specimen, said detecting means including means for generating an electrical signal having an amplitude related to the intensity of light leaving said selected point as a function of time, said generating means having a response time substantially less than the period of said predetermined frequency;

differential means for measuring the amplitude of the component of said electrical signal in a selected frequency band including said predetermined frequency;

integral means for measuring the amplitude of said electrical signal averaged over a time greater than one period of said predetermined frequency; and image generating means for causing said detecting means to select each of a plurality of preselected points and for displaying the ratio of the amplitudes measured by said differential and integral measuring means as a two dimensional image, wherein said detecting means includes:

means for imaging the light leaving said specimen on a surface;

means for detecting the intensity of light at the point on said surface corresponding to said selected point, and wherein said intensity detecting means includes an image dissector tube with its photocathode coincident with said surface.

* * * * *